Figure 1:
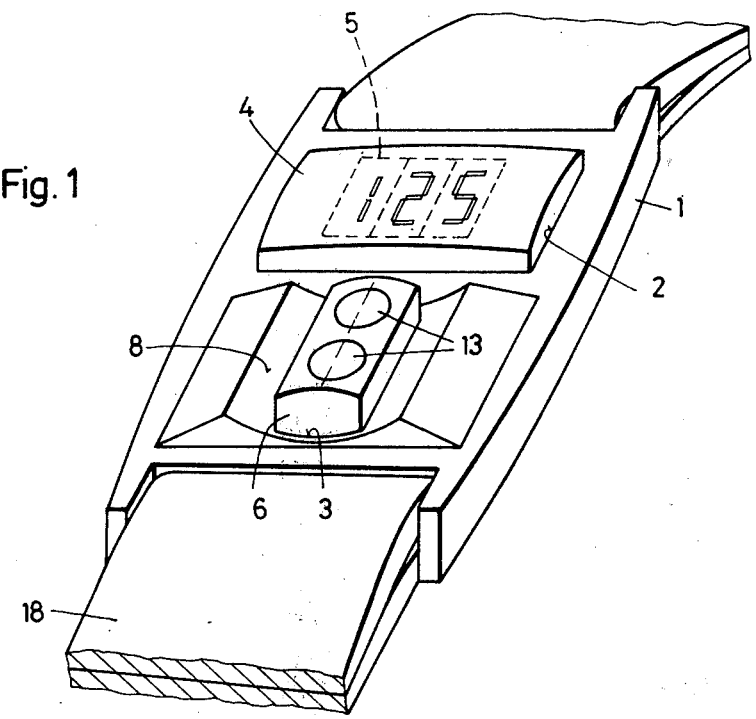

United States Patent [19]

Thalmann

[11] 4,129,124

[45] Dec. 12, 1978

[54] PULSE-RATE INDICATOR

[75] Inventor: René A. Thalmann, Starrkirch, Switzerland

[73] Assignee: Elektro-Apparatebau Olten A.G., Olten, Switzerland

[21] Appl. No.: 767,623

[22] Filed: Feb. 10, 1977

[30] Foreign Application Priority Data

Mar. 23, 1976 [CH] Switzerland ............ 3619/76

[51] Int. Cl.² ............................................. A61B 5/02
[52] U.S. Cl. ............................ 128/2.05 T; 128/2.05 D
[58] Field of Search ............ 128/2.05 F, 2 L, 2.05 R, 128/2.05 T, 2.05 P

[56] References Cited

U.S. PATENT DOCUMENTS 3,807,388  4/1974  Orr et al. .................... 128/2.05 R
3,908,636  9/1975  Page ........................... 128/2.05 T

FOREIGN PATENT DOCUMENTS 1426319  2/1976  United Kingdom ............ 128/2.05 R
311618  10/1971  U.S.S.R. ........................... 128/2 L

OTHER PUBLICATIONS

Hammer, W. E. et al., "Indirect Blood Pressure Finger Cuff", IBM Tech. Disclosure Bulletin, V. 8 #4, 9/65.

Primary Examiner—Robert W. Michell
Assistant Examiner—Francis J. Jaworski
Attorney, Agent, or Firm—Salter & Michaelson

[57] ABSTRACT

A pulse-rate indicator having electro-optical means for converting pulse beats into electric measuring pulses, means for generating a number of timing pulses derived from measuring pulses, means for calculating the pulse-rate from the number of timing pulses, means for displaying the pulse-rate, and a pushbutton for rendering the indicator operative, the electro-optical means being disposed in the pushbutton for generating the electric measuring pulses as a function of the perfusion of blood in a human fingertip pressing upon the pushbutton.

2 Claims, 5 Drawing Figures

PULSE-RATE INDICATOR

This invention relates to pulse-rate indicators, and more particularly to a pulse-rate indicator of the type having a current supply circuit, means for converting pulse beats into electric measuring pulses, and a pushbutton for rendering the indicator operative.

A known instrument for monitoring the pulse rate of a person engaging in a sport is disclosed in Swiss Pat. No. 526,296. The pulse beats are converted into electrical pulses by means of a sensor secured against the person's skin. A measuring circuit monitors the intervals between two successive pulses and generates a first signal when the interval is of a length corresponding to an adjustable maximum number of pulse beats, e.g., 180 beats per minute. This first signal causes an audible signal to sound, thus indicating to the wearer that he has reached his set limit of exertion. When the number of pulse beats drops below the set maximum, the audible signal ceases. The measuring circuit generates a second signal when the interval between two successive electrical pulses becomes greater than an adjustable minimum corresponding to the normal number of pulse beats, e.g., 78 beats per minute. This second signal causes another audible signal to sound, thus indicating to the wearer that he has recovered from the exertion. This known instrument enables the wearer to exercise intensively but within reasonable bounds.

It is an object of the present invention to provide an improved pulse-rate indicator of the type initially mentioned which, with a minimum of operating effort, furnishes an indication in digital form of the number of pulse beats per minute.

To this end, in the pulse-rate indicator according to the present invention, the improvement comprises electro-optical means disposed in the pushbutton for generating the electric measuring pulses as a function of the perfusion of blood in a human fingertip pressing upon the pushbutton, a measuring circuit for ascertaining the pulse rate per minute based on a predetermined number of electric measuring pulses, and digital indicating means for visibly displaying the ascertained pulse rate per minute.

Figure 2:
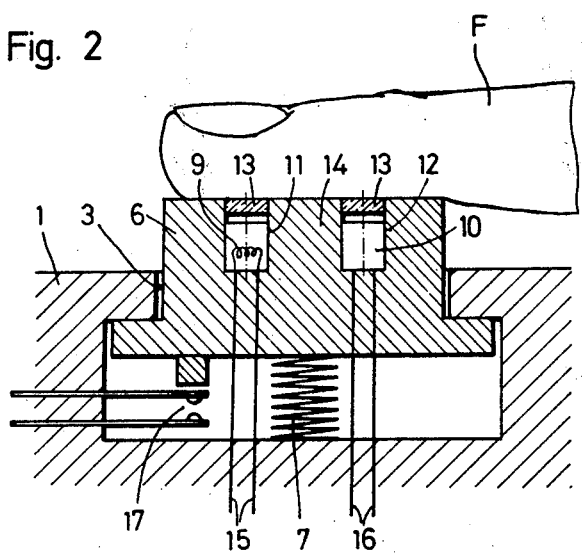
Figure 3:
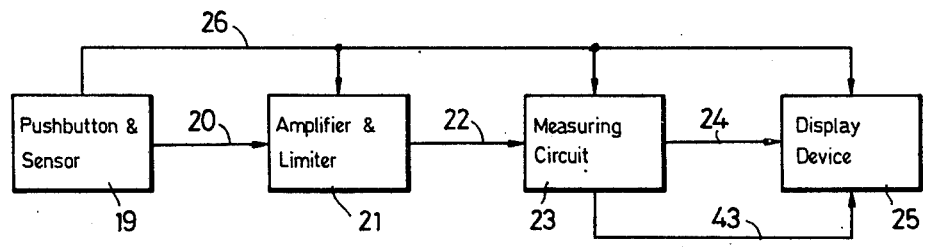
Figure 4:
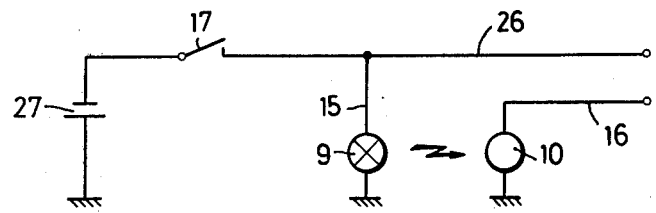
Figure 5:
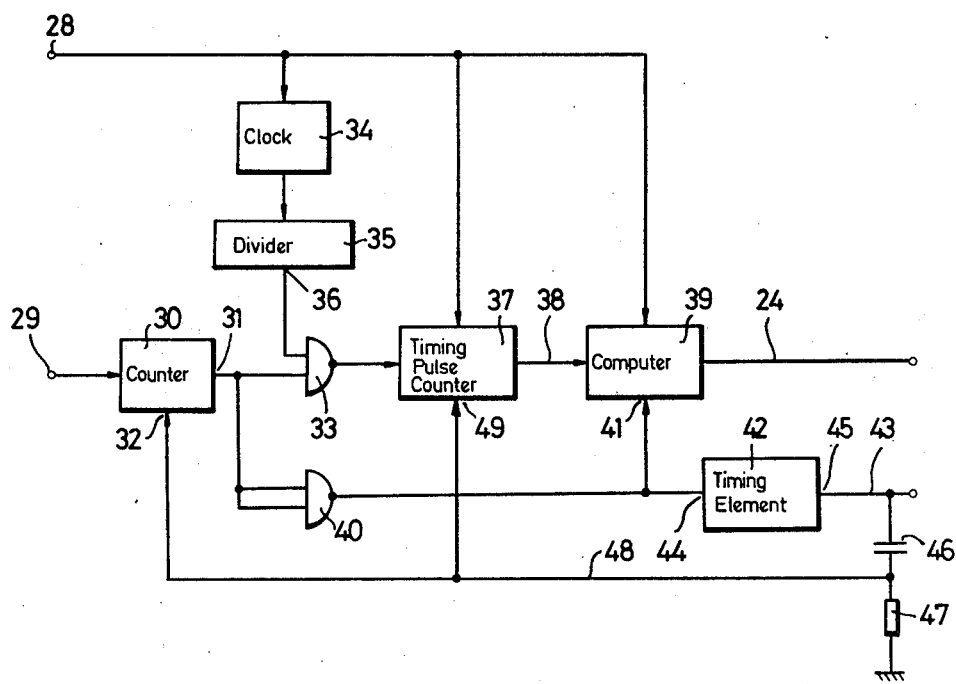

A preferred embodiment of the invention will now be described in detail with reference to the accompanying drawings, in which:

FIG. 1 is a perspective view of a pulse-rate indicator bearing a certain resemblance to a digital wristwatch, FIG. 2 is a diagrammatic sectional view through a pushbutton of the pulse-rate indicator illustrated in FIG. 1, FIG. 3 is a block diagram of the indicator of FIG. 1, FIG. 4 is a circuit diagram of the pushbutton and of an electro-optical device disposed therein, and FIG. 5 is a block diagram of a measuring circuit for ascertaining the number of pulse beats per minute.

The pulse-rate indicator illustrated in FIG. 1 has the outer appearance of a digital wristwatch. In a case 1, preferably made of metal, are a first aperture 2 and a second aperture 3. Aperture 2 is closed off by a glass window 4 through which three digital display elements 5, each comprising seven segments, are visible. Through aperture 3 there extends a portion of a pushbutton 6 which is displaceable within case 1 against the bias of a spring 7 visible in FIG. 2. The outwardly projecting portion of pushbutton 6 is situated in a depression 8, the shape of which is substantially adapted to that of a human finger F. The path of displacement of pushbutton 6 toward the interior of case 1 is limited by depression 8, so that the pressure of pushbutton 6 against finger F is independent of the force with which finger F is pressed into depression 8. This is important for the proper functioning of an electro-optical device comprising a light source 9 and a photosensitive element 10.

Light source 9 and photosensitive element 10, which may be a photoelement, a photodiode, or a phototransistor, are accommodated in recesses 11 and 12, respectively, in pushbutton 6. Recesses 11 and 12 are closed off by translucent plugs 13. Opaque material 14 between recesses 11 and 12 prevents light from light source 9 from reaching photosensitive element 10 directly. Light source 9 may be a miniature incandescent bulb or a light-emitting diode. When light source 9 emits light upon being supplied with electric current over connecting wires 15, and finger F is placed upon pushbutton 6, light penetrates into finger F, and part of that light is reflected to photosensitive element 10. The intensity of the light incident upon element 10 is dependent upon the perfusion of blood in finger F placed upon pushbutton 6. The perfusion of blood in finger F is influenced by the pulse. Hence the electric current flowing in connecting wires 16 of element 10 fluctuates in rhythm with the pulse.

Further associated with pushbutton 6 is an electric switch 17 which is closed when pushbutton 6 is operated. A bracelet or wrist-strap 18 is attached to case 1, as in a wristwatch.

FIG. 3 is a block diagram of the pulse-rate indicator illustrated in FIG. 1. The block designated as 19 symbolizes pushbutton 6 with the above-described electro-optical means acting as a sensor. Electrical currents dependent upon the pulse are supplied over a line 20 to an amplifier and limiter 21, at the output of which electric measuring pulses, preferably rectangular, appear in cadence with the pulse beats. These measuring pulses are conveyed via a line 22 to a measuring circuit 23, where they are processed, in a manner to be described in detail below with reference to FIG. 5, so that at the output of measuring circuit 23, the desired information signals appear, which are transmitted, preferably parallel over a multiple line 24, to a display device 25 containing the aforementioned digital display elements 5. Upon operation of pushbutton 6, a supply voltage is applied via switch 17 (FIG. 2) to a supply line 26, so that amplifier 21, measuring circuit 23, and display device 25 are ready for operation.

FIG. 4 illustrates the manner in which the components accommodated in pushbutton 6 are wired. Via switch 17, a battery 27, one pole of which is grounded, i.e., connected to case 1, can be connected to supply line 26. Further connected to supply line 26, over one of the wires 15, is light source 9, which lights up as soon as switch 17 is closed by operation of pushbutton 6. One of the wires 16 of photosensitive element 10 is grounded, while the other is connected to amplifier 21 over line 20.

FIG. 5 is a block diagram of measuring circuit 23. The supply voltage is fed to measuring circuit 23 via a terminal 28 connected to supply line 26. The measuring pulses produced by amplifier 21 reach the input of a counter 30 through an input terminal 29 of measuring circuit 23. Counter 30 comprises, for example, six active counting stages and is so constructed that it transmits a signal at its output 31 when it is reset and when it has counted to six. As soon as the first measuring pulse reaches the input of counter 30, the signal at output 31 disappears until the sixth measuring pulse has reached the input. Counter 30 remains at its sixth counting stage, regardless of whether further measuring pulses arrive, unit it is reset over its reset input 32. Output 31 of counter 30 is connected to one input of a two-input NAND gate 33 which is accordingly open during the time in which counter 30 counts from one to six.

Measuring circuit 23 further comprises a clock 34 which is preferably quartz-controlled for high accuracy. The relatively high pulse frequency of clock 34 is reduced in a divider 35 so that, for example, 100 timing pulses per second appear at output 36 of divider 35. These timing pulses arrive at the other input of NAND gate 33.

The timing pulses passed during the opening time of NAND gate 33 go from the latter to a timing-pulse counter 37, which is preferably a decimal coded binary counter having three decades. The number stored in timing-pulse counter 37 at the end of a measuring operation, i.e., when counter 30 has reached the sixth counting stage, is proportional to the time elapsed between the appearances of the first and sixth measuring pulses, which is five times the time T corresponding to the interval of occurrence of the pulse beats, as explained below.

The count of timing-pulse counter 37 is introduced via a multiple line 38 into a computer 39 and taken over by the latter at the end of the measuring operation. The end of the measuring operation is communicated to computer 39 via an inverter 40 and a control input 41. While counter 30 is counting, an enabling signal is applied to control input 41, causing the result previously calculated in computer 39 to be cleared readying computer 39 for taking over the next count of timing-pulse counter 37 at the end of the measuring operation.

In the present embodiment, computer 39 carries out a simple calculation at the end of each measuring operation in that it divides the preset number 30,000 by the count indicated by timing-pulse counter 37. The quotient thus calculated is the number of pulse beats per minute, which is supplied over multiple line 24 to display device 25 and displayed by the latter.

The duration of the display is determined by a timing element 42, to which the blocking signal from inverter 40 is likewise supplied during the counting operation of counter 30. As soon as the blocking signal disappears at input 44 of timing element 42, the latter produces a release signal at its output 45, e.g., for 5 seconds. This release signal is supplied to display device 25 over a line 43 and causes the result calculated by computer 39 to be visible during that length of time.

At the end of the release signal, there is produced by means of a differentiator, comprising a capacitor 46 and a resistor 47, a reset pulse which is supplied over a line 48 to a reset 49 of timing-pulse counter 37 and to reset input 32 of counter 30. By resetting of these two counters, a new measuring operation is initiated, provided pushbutton 6 is still being operated.

The above-mentioned preset number 30,000 which computer 39 divides by the count of timing-pulse counter 37 is determined by the mode of operation of measuring circuit 23. NAND gate 33 is open from the moment the first measuring pulse arrives until the appearance of the sixth measuring pulse, i.e., during five intervals. This corresponds to a duration of 5·T when T is the time in seconds between two successive pulse beats. During the opening time of NAND gate 33, 5·T·100 timing pulses have entered timing-pulse counter 37. In order to obtain the number of pulse beats per minute, it is necessary to carry out the division (60/T). However, the value 5·T·100 is stored in timing-pulse counter 37, so that it is accordingly necessary to calculate (60·500/5·T·100), i.e., 30,000 divided by the count of timing-pulse counter 37, in order to obtain the number of pulse beats per minute. This preset number varies with the number of measuring pulses counted by counter 30 and the frequency of the timing pulses supplied by NAND gate 33.

The measuring circuit described above yields precise measurements; although only whole pulse beats, no fractions thereof, are indicated, this is quite sufficient for normal needs.

If a longer measuring time and an indication error of up to 6% can be tolerated, a much simpler measuring circuit can be used. In such a simplified measuring circuit, counter 30 is dispensed with, i.e., the measuring pulses are supplied directly to NAND gate 33. Clock 34 and divider 35 are replaced by a timing element which opens NAND gate 33 for 10 seconds, for example. Timing-pulse counter 37 then counts the number of measuring pulses occurring during these 10 seconds. Computer 39 is replaced by a simple multiplier which multiplies the count of counter 37 by six. The product is already the number of pulse beats per minute to be ascertained and can be directly displayed.

Owing to the highly-developed miniaturization of the electronic components, the instrument described above can easily be accommodated in the space normally taken up by a wristwatch. It would also be possible to design case 1 of FIG. 1 like that of a small pocketwatch, in which form the described instrument would be suitable for use by nurses in taking the pulse of patients who would press pushbutton 6 with one of their fingers for this purpose.

Because of the ingenious combination of pushbutton 6 with the sensor and with switch 17, the pulse-rate indicator is in operation only when it is actually being used, thus saving wear and tear on battery 27.

What is claimed is:

1. A pulse rate indicator of the type having a current supply circuit, means for converting pulse beats into electric measuring pulses, and a pushbutton for operating said indicator, the improvement comprising a casing to which a strap is attached for mounting the casing on the wrist of the wearer, said pushbutton being mounted on said casing, said current supply circuit including a switch that is located in said casing and that is operable in response to depression of said pushbutton to close the circuit thereto, a measuring circuit located in said casing for ascertaining the pulse rate per minute based on a predetermined number of said electric measuring pulses, digital indicating means located in said casing and responsive to said measuring circuit for visually displaying the pulse rate per minute as ascertained by said measuring circuit, electro-optical means located in said pushbutton and being responsive to contact of a human fingertip therewith for generating said electric measuring pulses as a function of the perfusion of blood in said fingertip, said pushbutton having spaced recesses formed therein over which said fingertip is placed during the pulse measuring operation, said electro-optical means including a light source disposed in one of said recesses and a photosensitive element disposed in the other of said recesses, and means for controlling the pressure applied by said fingertip to said pushbutton so that sufficient pressure is applied to said pushbutton to close said switch and so that the pressure of the fingertip is limited in order to obtain a proper measurement of the perfusion of blood therein.

2. A pulse rate indicator as claimed in claim 1, said controlling means including a depression formed in said casing, through which said pushbutton extends, the configuration of said depression being generally concave and corresponding to the shape of the human fingertip for the accommodation thereof, wherein said depression limits the inward movement of said fingertip to provide for closing of said switch and for proper measurement of the perfusion of blood in said fingertip by said electro-optical means and measuring circuit.

* * * * *